US010806760B2

(12) United States Patent
Majeed et al.

(10) Patent No.: US 10,806,760 B2
(45) Date of Patent: Oct. 20, 2020

(54) COMPOSITIONS AND METHODS FOR REDUCING FLATULENCE

(71) Applicants: Muhammed Majeed, Edison, NJ (US); Kalyanam Nagabhushanam, East Windsor, NJ (US); Sivakumar Arumugam, Bangalore (IN); Furqan Ali, Bangalore (IN); Shaheen Majeed, Springville, UT (US)

(72) Inventors: Muhammed Majeed, Edison, NJ (US); Kalyanam Nagabhushanam, East Windsor, NJ (US); Sivakumar Arumugam, Bangalore (IN); Furqan Ali, Bangalore (IN); Shaheen Majeed, Springville, UT (US)

(73) Assignee: SAMI LABS LIMITED, Bangalore (IN)

( * ) Notice: Subject to any disclaimer, the term of this patent is extended or adjusted under 35 U.S.C. 154(b) by 159 days.

(21) Appl. No.: 15/995,393

(22) Filed: Jun. 1, 2018

(65) Prior Publication Data

US 2018/0353555 A1  Dec. 13, 2018

Related U.S. Application Data

(60) Provisional application No. 62/517,314, filed on Jun. 9, 2017.

(51) Int. Cl.
*A61K 35/742* (2015.01)
*A61P 1/14* (2006.01)
*C12N 1/20* (2006.01)
*C12R 1/07* (2006.01)

(52) U.S. Cl.
CPC .............. *A61K 35/742* (2013.01); *A61P 1/14* (2018.01); *C12N 1/20* (2013.01); *C12R 1/07* (2013.01)

(58) Field of Classification Search
CPC .......... A61K 35/742; C12R 1/07; C12N 1/20; A61P 1/14
See application file for complete search history.

(56) References Cited

U.S. PATENT DOCUMENTS

2009/0142315 A1* 6/2009 Farmer ................. A61K 35/742
424/93.46

OTHER PUBLICATIONS

Abhari et al., IJVR, 2015, vol. 16, No. 3, Ser. No. 52, p. 267-273.*
Guidelines for the evaluation of probiotics in food, Joint FAO/WHO Working Group Report on Drafting Guidelines for the Evaluation of Probiotics in Food, London, Ontario, Canada, Apr. 30 and May 1, 2002, section 3.1.
Probiotics: In Depth/NCCIH, U.S. Department of Health and Human Services (http://www.hhs.gov/) National Institutes of Health (http://www.nih.gov/), 2019.
Indian Council of Medical Research/Department of Biotechnology, Ministry of Science and Technology, Government of India, New Delhi), ICMR-DBT Guidelines for Evaluation of Probiotics in Food, 2011), Section 2, Subsection 2.3).
http://valentuschoice.com/ProDura-Comparison.pdf; https://earthnutri.com/pages/produra%C2%AE), 2020.
Mannu et al. (2003) International Journal of Food Microbiology 88 (2003) 291-304.
Castillo et. al., An evaluation of multidrug□resistant *Escherichia coli* isolates in urinary tract infections from Aguascalientes, Mexico: cross□sectional study, Ann Clin Microleiol Antimicrob (2018) 17:34.
Sabrina Montaña et al. 2016, The Genetic Analysis of an Acinetobacter johnsonii Clinical Strain Evidenced the Presence of Horizontal Genetic Transfer. PLoS One. 2016; 11(8): e0161528.
Gottlieb, K et al. 2015, Review article: inhibition of methanogenic archaea by statins as a targeted management strategy for constipation and related disorders. Aliment Pharmacol Ther. 2016 Jan. 2016; 43(2): 197-212.
Suzanne Devkota et al. 2012, Dietary-fat-induced taurocholic acid promotes pathobiont expansion and colitis in Il10-/- mice. Nature, 487, 104-108.
Baron EJ 1997, Bilophila wadsworthia: A unique Gram-negative anaerobic rod. Anaerobe. Apr.-Jun. 1997;3(2-3):83-6.
Nelson RL et al. 2017, Antibiotic treatment for Clostridium difficile-associated diarrhoea in adults. Cochrane Database Syst Rev. Mar. 3, 2017;3: CD004610.
Jay Marks, Intestinal Gas (Belching, Bloating, Flatulence; https://mwv.medicinenet.com/intestinal_gas_belching_bloating_flatulence/article.htm#intestinal_gas_definition_and_facts, accessed Apr. 4, 2018.
Davis and Cunha, Flatulence (Gas), https://www.emedicinehealth.com/flatulence__gas/article_em.htm, accessed Apr. 3, 2018.
Tuohy et al., Using probiotics and prebiotics to improve gut health, vol. 8, Issue 15, 2003, pp. 692-700.
Bailey et al., Effective management of flatulence, American family physician, Journal of the American academy of family physicians, https://mospace.umsystem.edu/xmlui/bitstream/handle/10355/3874/EffectiveManagementFlatulence.pdf?sequence=1&isAllowed=y, accessed Mar. 27, 2018.
Lawrence et al., Probiotics for recurrent Clostridium difficile disease, Sep. 1, 2005, Journal of Medical Microbiology 54: 905-906.
Quigley. Probiotics in the management of colonic disorders, Current Gastroenterology Reports, Oct. 2007, vol. 9, Issue 5, pp. 434 140.

(Continued)

*Primary Examiner* — Kade Ariani

(57) ABSTRACT

Disclosed are the methods and compositions for the reduction of intestinal gas/flatulence. Specifically a method for reducing flatulence using a composition containing probiotic bacteria *Bacillus coagulans* MTCC 5856 is disclosed. More specifically, the invention discloses a method for inhibiting the growth of microorganisms that facilitate the production of intestinal gas, using a composition containing probiotic bacteria *Bacillus coagulans* MTCC 5856.

9 Claims, 1 Drawing Sheet

(56) References Cited

OTHER PUBLICATIONS

Egle Cekanaviciute et al. 2017, Gut bacteria from multiple sclerosis patients modulate human T cells and exacerbate symptoms in mouse models. Proc Nati Aced Sci U S A; 114(40): 10713-10718.
Hughes LE, et al. 2003, Cross-reactivity between related sequences found in *Acinetobacter* sp., Pseudomonas aeruginosa, myelin basic protein and myelin oligodendrocyte glycoprotein in multiple sclerosis. J Neuroimmunol 144:105-115.

* cited by examiner

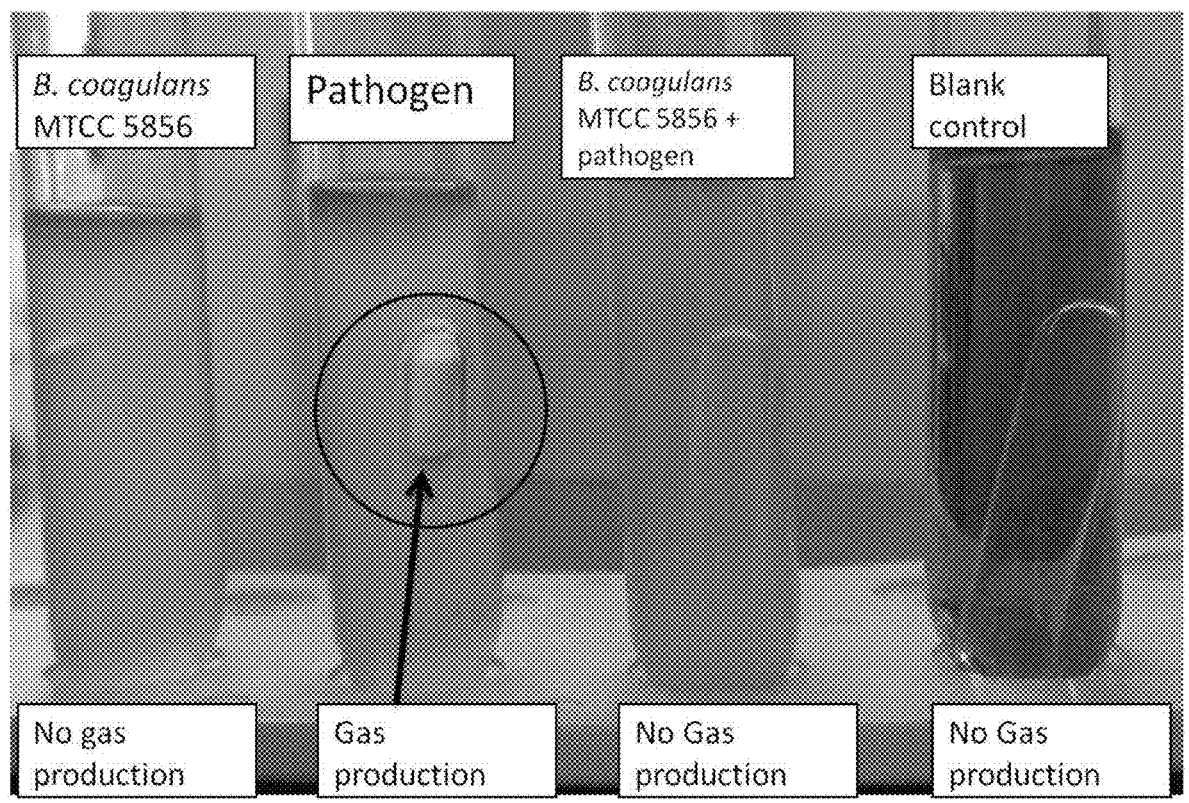

COMPOSITIONS AND METHODS FOR REDUCING FLATULENCE

CROSS-REFERENCE TO RELATED APPLICATIONS

This is a non-provisional application claiming priority from U.S. provisional application No. 62/517,314 filed on 9 Jun. 2017.

BACKGROUND OF THE INVENTION

Field of the Invention

The present invention in general relates to flatulence reduction. More specifically, the present invention relates to a composition containing probiotic bacteria *Bacillus coagulans* and methods thereof for the reduction of intestinal gas and inhibiting gas producing microorganisms.

Description of Prior Art

Intestinal gas or flatulence is a biological process wherein excess gas collects in the digestive system, as a result of swallowing too much air while drinking and eating. Gas also gets accumulated as a result of the normal digestive process due to fermentation of food stuff. The body gets rid of the excess gas by farting (flatulence) or burping (belching). Sometimes, excessive flatulence indicate an underlying health condition such as irritable bowel syndrome, indigestion, constipation, cramps, bloating, diarrhea, coeliac disease, lactose intolerance, gastroenteritis and giardiasis—an infection of the digestive system caused by microbes.

The presence of pathogenic microbes in the gut also increases the frequency of flatulence. Intestinal microbes which include, but not limited to, *E. coli, Clostridium difficile Acinetobacter calcoaceticus, Acinetobacter johnsonii, Methanobrevibacter smithii*, and *Bilophila wadsworthia* etc., increase the intestinal gas by fermenting undigested food stuff.

*Acinetobacter calcoaceticus* is a non-motile, Gram negative coccobacillus, bacterial species of the genus *Acinetobacter*. It is catalase positive and oxidase negative and grows under aerobic conditions and considered to be the part of the normal human intestinal flora. However, all *Acinetobacter* species, including *Acinetobacter baumannii, Acinetobacter calcoaceticus*, and *Acinetobacter lwoffii*, are rare in the healthy human gut. Furthermore, a recent study concluded that the increase in the number of *Acinetobacter calcoaceticus* in the gut may be associated with the pathogenesis of multiple sclerosis (Egle Cekanaviciute et al. 2017, Gut bacteria from multiple sclerosis patients modulate human T cells and exacerbate symptoms in mouse models. Proc Natl Acad Sci U S A; 114(40): 10713-10718.; Hughes L E, et al. 2003, Cross-reactivity between related sequences found in *Acinetobacter* sp., *Pseudomonas aeruginosa*, myelin basic protein and myelin oligodendrocyte glycoprotein in multiple sclerosis. J Neuroimmunol 144:105-115).

*Acinetobacter johnsonii* is usually found in the environment and animals. It can occasionally colonize human skin and cause clinical infections such as catheter-related bloodstream infections or peritonitis associated with peritoneal dialysis (Sabrina Montaña et al. 2016, The Genetic Analysis of an *Acinetobacter johnsonii* Clinical Strain Evidenced the Presence of Horizontal Genetic Transfer. PLoS One. 2016; 11(8): e0161528).

*Methanobrevibacter smithii*, a methane-producing bacterial species, is a single-celled microorganism from the Archaea domain which is commonly found in the gut of healthy humans and contributes to 10% of all anaerobes (oxygen-hating bacteria) in the colon. It is considered to be the key gut microbe that aids digestion, specifically by breaking down complex carbohydrates. It facilitates digestion by combining hydrogen with carbon dioxide to produce methane, while supporting the extraction of energy from nutrients. Studies show a strong association between delayed intestinal transit and the production of methane. Experimental data suggest a direct inhibitory activity of methane on the colonic and ileal smooth muscle and a possible role for methane as a gasotransmitter. Thus, in general, higher levels of methanogens can be associated with constipation (Gottlieb, K et al. 2015, Review article: inhibition of methanogenic archaea by statins as a targeted management strategy for constipation and related disorders. Aliment Pharmacol Ther. 2016 January; 43(2): 197-212). *M. smithii* also scavenges hydrogen from other microbes and use it to produce methane. This interaction may help neighbouring hydrogen-producing bacteria to thrive and extract nutrients from food more efficiently. Thus, this may contribute to weight gain. Moreover, in a human study, the presence of both methane and hydrogen on breath testing was associated with increased BMI and percent body fat in humans. Hence, inhibiting the growth/number of *M. smithii* and the production of gases (methane and hydrogen) while fermenting the various carbon sources including prebiotic fibres could be a target to control and prevent the constipation and weight gain associated with the gut colonization of *M. smithii*.

*Bilophila wadsworthia* is the third most common anaerobe recovered from clinical material obtained from patients with perforated and gangrenous appendicitis. However, *Bilophila wadsworthia* contributes to less than 0.01% of the normal human gastrointestinal microbiota but the increase in the number of this organism was observed in multiple disease conditions. The increase in the number of *Bilophila wadsworthia* (zero to 6 percent) was observed when mice were fed with milk fat which lead to the development immune-mediated disease like inflammatory bowel disease. The bacteria produce substances that irritate the gut lining and make it more porous, admitting immune cells that trigger inflammation (Suzanne Devkota et al. 2012, Dietary-fat-induced taurocholic acid promotes pathobiont expansion and colitis in Il10−/− mice. Nature, 487, 104-108). *B. wadsworthia* has been recovered from clinical specimens associated with a variety of infections, including sepsis, liver abscesses, cholecystitis, Fournier's gangrene, soft tissue abscesses, empyema, osteomyelitis, Bartholinitis, and hidradenitis suppurativa. In addition, it has been found in the saliva and vaginal fluids of asymptomatic adults and even in the periodontal pockets of dogs (Baron E J 1997, *Bilophila wadsworthia*: a unique Gram-negative anaerobic rod. Anaerobe. 1997 April-June; 3(2-3):83-6).

*Clostridium difficile* often called *C. difficile* or *C. diff*, is anaerobic, motile, ubiquitous, Gram-positive, spore-forming bacterium which causes symptomatic infections such as watery diarrhea, fever, nausea, and abdominal pain. It makes up about 20% of cases of antibiotic-associated diarrhea. Complications may include pseudomembranous colitis, toxic megacolon, perforation of the colon, bloating, or blood in stool and sepsis (Nelson R L et al. 2017, Antibiotic treatment for *Clostridium difficile*-associated diarrhoea in adults. Cochrane Database Syst Rev. 2017 Mar. 3; 3: CD004610).

All the above microbes, increase the production of intestinal gas thereby leading to bloating, abdominal discomfort and distension, excessive gas pressure and belching, irritable bowel syndrome, diarrhea, coeliac disease, gastroenteritis etc., (Jay Marks, Intestinal Gas (Belching, Bloating, Flatulence), www.medicinenet.com/intestinal_gas_belching_bloating_flatulence/article.htm#intestinal_gas_definition_and_facts, accessed 4 Apr. 2018; Davis and Cunha, Flatulence (Gas), www.emedicinehealth.com/flatulence_gas/article_em.htm, accessed 3 Apr. 2018)

Probiotics are gaining importance as a dietary supplement owing to their ability to modify the gut microflora for yielding increased health benefits. Reports indicate that probiotic administration has positive effects on the inhibition of the growth of pathogenic microbes that facilitate increased flatulence. This is evident in the following prior art documents
1. Tuohy et al., Using probiotics and prebiotics to improve gut health, Volume 8, Issue 15, 2003, Pages 692-700;
2. Bailey et al., Effective management of flatulence, American family physician, Journal of the American academy of family physicians, mospace.umsystem.edu/xmlui/bitstreanm/handle/10355/3874/EffectiveManagementFlatulence.pdf?sequence=1&isAllowed=y, accessed 27 Mar. 2018)
3. Lawrence et al., Probiotics for recurrent *Clostridium difficile* disease, 1 Sep. 2005, Journal of Medical Microbiology 54: 905-906.
4. Quigley. Probiotics in the management of colonic disorders, Current Gastroenterology Reports, October 2007, Volume 9, Issue 5, pp 434-440

However, there still exists an unmet industrial need for a probiotic that is effective against most of the pathogenic microbes in the gut. Also, it is well known in the scientific art that biological effects of probiotics or products thereof are strain specific and cannot be generalised among genera, species and strains (Probiotics: In Depth/NCCIH, U.S. Department of Health and Human Services, National Institutes of Health). Hence, there exists a need to find a probiotic strain that is more efficient and viable against the pathogenic microbes that increase gas production in the intestines. The present invention solves the above technical problem by disclosing a probiotic strain that is viable and efficient in controlling the intestinal gas.

The principle objective of the inventions is to disclose a method for the reduction of intestinal gas using a composition comprising *Bacillus coagulans*.

It is another objective of the inventions to disclose a method for inhibiting the growth of micro-organisms that facilitate the production of intestinal gas using compositions comprising *Bacillus coagulans*.

It is yet another objective of the invention to disclose a composition containing *Bacillus coagulans* that produces substantially less or no intestinal gas/flatulence when it ferments the carbohydrate source or prebiotic fibre.

The present invention fulfils aforesaid objectives and provides further related advantages.

DEPOSIT OF BIOLOGICAL MATERIAL

The deposit of biological material *Bacillus coagulans* SBC37-01 bearing accession number MTCC 5856, mentioned in the instant application has been made on 19 Sep. 2013 at Microbial Type Culture Collection & Gene Bank (MTCC), CSIR-Institute of Microbial Technology, Sector 39-A, Chandigarh—160036, India.

SUMMARY OF THE INVENTION

The present invention discloses methods and compositions for the reduction of intestinal gas/flatulence. Specifically the invention discloses a method for reducing flatulence using a composition containing probiotic bacteria *Bacillus coagulans* MTCC 5856. More specifically, the invention discloses a method for inhibiting the growth of microorganisms that facilitate the production of intestinal gas, using a composition containing probiotic bacteria *Bacillus coagulans* MTCC 5856.

BRIEF DESCRIPTION OF THE FIGURES

FIG. 1, shows the illustrative representation of the experimental procedure to evaluate the inhibition of gas production of pathogens by the probiotic strain *Bacillus coagulans* MTCC 5856.

DESCRIPTION OF THE MOST PREFERRED EMBODIMENTS

In a principle embodiment, the present invention discloses a method for reducing gas formed as a by-product of microbial fermentation, said method comprising steps of co-culturing the gas producing microbes with a probiotic bacteria *Bacillus coagulans*, in the presence of media containing carbohydrate source and prebiotic fibres, to bring about the reduction in gas formation. In a related embodiment, the probiotic bacteria *Bacillus coagulans* per se does not produce substantial gas/flatus when cultured with carbohydrate source and prebiotic fibres. In a related embodiment, the *Bacillus coagulans* is in the form of spore and/or a vegetative cell. In a related embodiment, the strain of *Bacillus coagulans* is selected from the group consisting of *Bacillus coagulans* MTCC 5856, *Bacillus coagulans* ATCC 31284 and *Bacillus coagulans* ATCC 7050. In another preferred embodiment, the gas producing microbes are selected from the list consisting of *E. coli, Acinetobacter baumannii, Acinetobacter calcoaceticus, Acinetobacter lwoffii, Acinetobacter johnsonii, Methanobrevibacter smithii, Bilophila wadsworthia*, and *Clostridium difficile*. In another related embodiment, the carbohydrate source and prebiotic fibres are selected form the group consisting of fructo-oligosaccharide (FOS), Galacto-oligosaccharide (GOS), Lactose, potato starch, Inulin, polydextrose and dextrose.

In another preferred embodiment, the present invention discloses a method for inhibiting the growth of gas producing microbes, said method comprising steps of co-culturing the gas producing microbes with a probiotic bacteria *Bacillus coagulans*, in the presence of media containing carbohydrate source and prebiotic fibre, to bring about the reduction in the viable colonies of gas producing microbes. In a related embodiment, the *Bacillus coagulans* is in the form of spore and/or a vegetative cell. In a related embodiment, the strain of *Bacillus coagulans* is selected from the group consisting of *Bacillus coagulans* MTCC 5856, *Bacillus coagulans* ATCC 31284 and *Bacillus coagulans* ATCC 7050. In another preferred embodiment, the gas producing microbes are selected from the list consisting of *E. coli, Acinetobacter baumannii, Acinetobacter calcoaceticus*, and *Acinetobacter lwoffii, Acinetobacter johnsonii, Methanobrevibacter smithii, Bilophila wadsworthia*, and *Clostridium*

*difficile*. In another related embodiment, the carbohydrate source and prebiotic fibres are selected form the group consisting of fructo-oligosaccharide (FOS), Galacto-oligosaccharide (GOS), Lactose, potato starch, Inulin, polydextrose and dextrose.

In yet another preferred embodiment, the invention discloses a method of reducing flatus (intestinal gas), formed as a byproduct of bacterial fermentation in mammalian gastrointestinal tract, said method comprising step of administering an effective dose of a composition containing *Bacillus coagulans* to bring about the effect of reducing volume of flatus formed. In a related embodiment, the probiotic bacteria *Bacillus coagulans* per se does not produce substantial flatus when administered individually or in combination with carbohydrate source and prebiotic fibres. In a related embodiment, the *Bacillus coagulans* is in the form of spore and/or a vegetative cell. In a related embodiment, the strain of *Bacillus coagulans* is selected from the group consisting of *Bacillus coagulans* MTCC 5856, *Bacillus coagulans* ATCC 31284 and *Bacillus coagulans* ATCC 7050. In another related embodiment, the reduction of flatus formation brings about reduction in bloating and/or bloating before it starts, abdominal discomfort and distension, excessive gas pressure and belching, diarrhea, coeliac disease, gastroenteritis in said mammals. In another preferred embodiment, the flatus producing bacteria are selected from the list consisting of *E. coli, Acinetobacter baumannii, Acinetobacter calcoaceticus, Acinetobacter lwoffii, Acinetobacter johnsonii, Methanobrevibacter smithii, Bilophila wadsworthia,* and *Clostridium difficile*. In another related embodiment, the effective dose of *Bacillus coagulans* is $1\times10^6$ to $1\times10^{14}$ cfu. In another related embodiment, the effective dose of *Bacillus coagulans* is preferably $2\times10^9$ cfu. In a related embodiment, the composition is formulated with pharmaceutically/nutraceutically acceptable excipients, adjuvants, diluents or carriers and administered in the form of tablets, capsules, syrups, gummies, powders, suspensions, emulsions, chewables, candies and eatables. In a related embodiment, the mammal is preferably human.

In another preferred embodiment, the invention discloses a method of reducing the numbers of flatus (intestinal gas) causing bacteria in the mammalian gastrointestinal tract, said method comprising step of administering an effective dose of a composition containing *Bacillus coagulans* to bring about the effect of reduction in the viable colonies of flatus causing bacteria in mammalian gastrointestinal tract. In a related embodiment, the *Bacillus coagulans* is in the form of spore and/or a vegetative cell. In a related embodiment, the strain of *Bacillus coagulans* is selected from the group consisting of *Bacillus coagulans* MTCC 5856, *Bacillus coagulans* ATCC 31284 and *Bacillus coagulans* ATCC 7050. In another related embodiment, the reduction of flatus forming bacteria brings about reduction in bloating and/or bloating before it starts, abdominal discomfort and distension, excessive gas pressure and belching, diarrhea, coeliac disease, gastroenteritis in said mammals. In another preferred embodiment, the flatus producing microbes are selected from the list consisting of *E. coli, Acinetobacter baumannii, Acinetobacter calcoaceticus, Acinetobacter lwoffii, Acinetobacter johnsonii, Methanobrevibacter smithii, Bilophila wadsworthia,* and *Clostridium difficile*. In another related embodiment, the effective dose of *Bacillus coagulans* is $1\times10^6$ to $1\times10^{14}$ cfu. In another related embodiment, the effective dose of *Bacillus coagulans* is preferably $2\times10^9$ cfu. In a related embodiment, the composition is formulated with pharmaceutically/nutraceutically acceptable excipients, adjuvants, diluents or carriers and administered in the form of tablets, capsules, syrups, gummies, powders, suspensions, emulsions, chewables, candies and eatables. In a related embodiment, the mammal is preferably human.

The aforesaid most preferred embodiments incorporating the technical features and technical effects of instant invention, are explained through illustrative examples herein under.

Example 1: Materials and Methods

De Man, Rogosa and Sharpe (MRS) media was used to evaluate the gas production and inhibition of pathogens by the probiotic strain *Bacillus coagulans* MTCC 5856. To study the gas production using different carbon sources along with prebiotic fibres, dextrose was replaced in the MRS media by supplementing with galacto-oligosaccharides (GOS), fructooligosaccharides (FOS), Lactose, potato soluble starch, inulin and polydextrose in different set of experiments. In a test tube 10 ml of media a Durham tube a smaller inverted tube which can serve as a trap for gas bubbles generated during fermentation, was placed. Microorganisms including *Escherichia coli, Acinetobacter calcoaceticus, Acinetobacter johnsonii, Methanobrevibacter smithii, Clostridium difficile, Bilophila wadsworthia* were studied in a co-culture model along with probiotic strain *B. coagulans* MTCC 5856. *Escherichia coli, Acinetobacter calcoaceticus* and *Acinetobacter johnsonii* were grown in trypticase soya broth and *E. coli* and *Acinetobacter calcoaceticus* and *Acinetobacter johnsonii* were enumerated in Eosin methylene blue agar and trypticase soya agar respectively. *Methanobrevibacter smithii, Clostridium difficile, Bilophila wadsworthia* were grown in Wilkins Chalgren broth supplemented with 5% fetal calf bovine. Overnight grown culture of *B. coagulans* MTCC 5856 was inoculated in different sets of test tube containing 10 ml of media (supplemented with different carbon source along with prebiotic fibres) along with Durham tube. Further, each set was inoculated with different pathogens and incubated at 37° C. in an anaerobic environment using Anaerobic workstation (Imset, India). After incubation, tubes were observed for visible gas production. For each carbon source and each pathogen, respective controls were taken where one tube had only *B. coagulans* MTCC 5856 and one tube had only pathogenic microbes. The third tube was inoculated with both *B. coagulans* MTCC 5856 and pathogens. In a similar set of experiment, viable counts of pathogens were estimated on respective selective agar media using a plate count method.

Example 2: Reduction of Gas Production by *B. coagulans* MTCC 5856

Table 1-6 shows the results of reduction of gas by *B. coagulans* MTCC 5856 formed due to the presence of pathogenic microbes *E. coli* ATCC 8739, *Acinetobacter calcoaceticus* ATCC 23055, *Acinetobacter johnsonii* NCIMB9871, *Methanobrevibacter smithii* DSM-861, *Clostridium difficile* ATCC 9689, *Bilophila wadsworthia* ATCC 49260 using GOS, FOS, Lactose, Starch as substrate

TABLE 1

Gas production by *B. coagulans* MTCC 5856 and *E. coli* ATCC 8739 alone and in combination using GOS, FOS, Lactose, Starch as substrate

| S. No. | Media composition | *B. coagulans* MTCC 5856 alone | *E. coli* ATCC 8739 alone | *B. coagulans* MTCC 5856 + *E. coli* ATCC 8739 |
|---|---|---|---|---|
| 1. | MRSD + FOS | − | ++ | − |
| 2. | MRSD + GOS | − | ++ | − |
| 3. | MRSD + Lactose | − | +++ | + |
| 4. | MRSD + Potato Starch | − | ++ | − |
| 5. | MRSD + Inulin | − | ++ | − |
| 6. | MRSD + Polydextrose | − | +++ | + |
| 7. | MRSD + Dextrose | − | +++ | + |

−, No Gas production
+, Minimal gas production (small bubble in Durham tube)
++, Substantial amount of gas production (half Durham tube filled with gas bubble)
+++, Excess amount of gas production (almost 90% of Durham tube filled with gas bubble).
MRSD is the MRS media devoid of dextrose

TABLE 2

Gas production by *B. coagulans* MTCC 5856 and *Acinetobacter calcoaceticus* ATCC 23055 alone and in combination using GOS, FOS, Lactose, and Starch as substrate

| S. No. | Media composition | *B. coagulans* MTCC 5856 alone | *A. calcoaceticus* ATCC 23055 alone | *B. coagulans* MTCC 5856 + *A. calcoaceticus* ATCC 23055 |
|---|---|---|---|---|
| 1 | MRSD + FOS | − | ++ | − |
| 2 | MRSD + GOS | − | ++ | − |
| 3 | MRSD + Lactose | − | ++ | − |
| 4 | MRSD + Potato Starch | − | ++ | − |
| 5 | MRSD + Inulin | − | ++ | − |
| 6 | MRSD + Polydextrose | − | ++ | − |
| 7 | MRSD + Dextrose | − | ++ | − |

−, No Gas production
+, Minimal gas production (small bubble in Durham tube)
++, Substantial amount of gas production (half Durham tube filled with gas bubble)
+++, Excess amount of gas production (almost 90% of Durham tube filled with gas bubble).

TABLE 3

Gas production by *B. coagulans* MTCC 5856 and *Acinetobacter johnsonii* NCIMB9871 alone and in combination using GOS, FOS, Lactose, Starch as substrate

| S. No. | Media composition | *B. coagulans* MTCC 5856 alone | *A. johnsonii* NCIMB9871 alone | *B. coagulans* MTCC 5856 + *A. johnsonii* NCIMB9871 |
|---|---|---|---|---|
| 1 | MRSD + FOS | − | ++ | − |
| 2 | MRSD + GOS | − | ++ | − |
| 3 | MRSD + Lactose | − | ++ | − |
| 4 | MRSD + Potato Starch | − | ++ | − |
| 5 | MRSD + Inulin | − | ++ | − |
| 6 | MRSD + Polydextrose | − | +++ | − |
| 7 | MRSD + Dextrose | − | +++ | + |

−, No Gas production
+, Minimal gas production (small bubble in Durham tube)
++, Substantial amount of gas production (half Durham tube filled with gas bubble)
+++, Excess amount of gas production (almost 90% of Durham tube filled with gas bubble).

TABLE 4

Gas production by *B. coagulans* MTCC 5856 and *Methanobrevibacter smithii* DSM-861 alone and in combination using GOS, FOS, Lactose, Starch as substrate

| S. No. | Media composition | *B. coagulans* MTCC 5856 alone | *Methanobrevibacter smithii* DSM-861 alone | *B. coagulans* MTCC 5856 + *Methanobrevibacter smithii* DSM-861 |
|---|---|---|---|---|
| 1 | MRSD + FOS | − | ++ | − |
| 2 | MRSD + GOS | − | ++ | − |
| 3 | MRSD + Lactose | − | ++ | − |
| 4 | MRSD + Potato Starch | − | ++ | − |
| 5 | MRSD + Inulin | − | ++ | − |
| 6 | MRSD + Polydextrose | − | ++ | − |
| 7 | MRSD + Dextrose | − | +++ | − |

−, No Gas production
+, Minimal gas production (small bubble in Durham tube)
++, Substantial amount of gas production (half Durham tube filled with gas bubble)
+++, Excess amount of gas production (almost 90% of Durham tube filled with gas bubble).
MRSD is the MRS media devoid of dextrose

TABLE 5

Gas production by *B. coagulans* MTCC 5856 and *Clostridium difficile* ATCC 9689 alone and in combination using GOS, FOS, Lactose, Starch as substrate

| S. No. | Media composition | *B. coagulans* MTCC 5856 alone | *Clostridium difficile* ATCC 9689 alone | *B. coagulans* MTCC 5856 + *Clostridium difficile* ATCC 9689 |
|---|---|---|---|---|
| 1 | MRSD + FOS | − | +++ | + |
| 2 | MRSD + GOS | − | ++ | − |
| 3 | MRSD + Lactose | − | ++ | − |
| 4 | MRSD + Potato Starch | − | ++ | − |
| 5 | MRSD + Inulin | − | ++ | − |
| 6 | MRSD + Polydextrose | − | ++ | + |
| 7 | MRSD + Dextrose | − | +++ | + |

−, No Gas production
+, Minimal gas production (small bubble in Durham tube)
++, Substantial amount of gas production (half Durham tube filled with gas bubble)
+++, Excess amount of gas production (almost 90% of Durham tube filled with gas bubble).
MRSD is the MRS media devoid of dextrose

TABLE 6

Gas production by *B. coagulans* MTCC 5856 and *Bilophila wadsworthia* ATCC 49260 alone and in combination using GOS, FOS, Lactose, Starch as substrate

| S. No. | Media composition | *B. coagulans* MTCC 5856 alone | *B. wadsworthia* ATCC 49260 alone | *B. coagulans* MTCC 5856 + *B. wadsworthia* ATCC 49260 |
|---|---|---|---|---|
| 1 | MRSD + FOS | − | ++ | − |
| 2 | MRSD + GOS | − | ++ | − |
| 3 | MRSD + Lactose | − | ++ | − |

TABLE 6-continued

Gas production by *B. coagulans* MTCC 5856 and *Bilophila wadsworthia* ATCC 49260 alone and in combination using GOS, FOS, Lactose, Starch as substrate

| S. No. | Media composition | *B. coagulans* MTCC 5856 alone | *B. wadsworthia* ATCC 49260 alone | *B. coagulans* MTCC 5856 + *B. wadsworthia* ATCC 49260 |
|---|---|---|---|---|
| 4 | MRSD + Potato Starch | – | ++ | – |
| 5 | MRSD + Inulin | – | ++ | – |
| 6 | MRSD + Polydextrose | – | ++ | – |
| 7 | MRSD + Dextrose | – | ++ | – |

–, No Gas production
+, Minimal gas production (small bubble in Durham tube)
++, Substantial amount of gas production (half Durham tube filled with gas bubble)
+++, Excess amount of gas production (almost 90% of Durham tube filled with gas bubble).
MRSD is the MRS media devoid of dextrose The results indicated that *B. coagulans* MTCC 5856 significantly reduced the gas produced by the pathogenic microbes *E. coli* ATCC 8739, *Acinetobacter calcoaceticus* ATCC 23055, *Acinetobacter johnsonii* NCIMB9871, *Methanobrevibacter smithii* DSM-861, *Clostridium difficile* ATCC 9689, *Bilophila wadsworthia* ATCC 49260 when it was co-fermented using GOS, FOS, Lactose, as substrate. The results also indicated that *B. coagulans* MTCC 5856 alone did not produce any gas when cultured in media containing carbohydrate source and prebiotic fibres.

Example 3: Effect of *B. coagulans* MTCC 5856 on the Viable Count of Gas Producing Microbes Tables 7-12 depict the effect of *Bacillus coagulans* MTCC 5856 on the growth and viable count of flatus producing microbes *E. coli* ATCC 8739, *Acinetobacter calcoaceticus* ATCC 23055, *Acinetobacter johnsonii* NCIMB9871, *Methanobrevibacter smithii* DSM-861, *Clostridium difficile* ATCC 9689, *Bilophila wadsworthia* ATCC 49260.

TABLE 7

Effect of *B. coagulans* MTCC 5856 on the viable count of *E. coli* ATCC 8739

| S. No. | Media composition | *E. coli* ATCC 8739 alone (cfu/ml) | *B. coagulans* MTCC 5856 + *E. coli* ATCC 8739 (cfu/ml) |
|---|---|---|---|
| 1 | MRSD + FOS | 8.3222 ± 0.11 | 5.8750 ± 0.12 |
| 2 | MRSD + GOS | 8.7708 ± 0.14 | 6.3979 ± 0.13 |
| 3 | MRSD + Lactose | 8.6741 ± 0.12 | 5.9294 ± 0.11 |
| 4 | MRSD + Potato Starch | 8.5471 ± 0.13 | 5.5440 ± 0.14 |
| 5 | MRSD + Inulin | 8.5647 ± 0.13 | 5.1760 ± 0.18 |
| 6 | MRSD + Polydextrose | 8.7411 ± 0.12 | 5.3971 ± 0.16 |
| 7 | MRSD + Dextrose | 8.8578 ± 0.10 | 5.5440 ± 0.11 |

TABLE 8

Effect of *B. coagulans* MTCC 5856 on the viable count of *A. calcoaceticus* ATCC 23055

| S. No. | Media composition | *A. calcoaceticus* ATCC 23055 alone (cfu/ml) | *B. coagulans* MTCC 5856 + *A. calcoaceticus* ATCC 23055 (cfu/ml) |
|---|---|---|---|
| 1 | MRSD + FOS | 8.5682 ± 0.12 | 5.8751 ± 0.14 |
| 2 | MRSD + GOS | 8.6232 ± 0,11 | 5.8971 ± 0.10 |
| 3 | MRSD + Lactose | 8.3222 ± 0.13 | 5.7993 ± 0.11 |
| 4 | MRSD + Potato Starch | 8.4313 ± 0.14 | 5.6544 ± 0.12 |
| 5 | MRSD + Inulin | 8.3979 ± 0.11 | 5.3761 ± 0.15 |
| 6 | MRSD + Polydextrose | 8.4712 ± 0.10 | 5.4391 ± 0.11 |
| 7 | MRSD + Dextrose | 8.7708 ± 0.14 | 5.6540 ± 0.12 |

TABLE 9

Effect of *B. coagulans* MTCC 5856 on the viable count of *A. johnsonii* NCIMB9871

| S. No. | Media composition | *A. johnsonii* NCIMB9871 alone (cfu/ml) | *B. coagulans* MTCC 5856 + *A. johnsonii* NCIMB9871 (cfu/ml) |
|---|---|---|---|
| 1 | MRSD + FOS | 8.7631 ± 0.11 | 5.7872 ± 0.16 |
| 2 | MRSD + GOS | 8.8238 ± 0.12 | 5.9732 ± 0.14 |
| 3 | MRSD + Lactose | 8.4323 ± 0.15 | 5.8791 ± 0.10 |
| 4 | MRSD + Potato Starch | 8.6438 ± 0.14 | 5.7643 ± 0.12 |
| 5 | MRSD + Inulin | 8.4392 ± 0.10 | 5.4765 ± 0.15 |
| 6 | MRSD + Polydextrose | 8.3723 ± 0.10 | 5.3382 ± 0.15 |
| 7 | MRSD + Dextrose | 8.8701 ± 0.11 | 5.8326 ± 0.11 |

TABLE 10

Effect of *B. coagulans* MTCC 5856 on the viable count of *Methanobrevibacter smithii* DSM-861

| S. No. | Media composition | *M. smithii* DSM-861 alone (cfu/ml) | *B. coagulans* MTCC 5856 + *M. smithii* DSM-861 (cfu/ml) |
|---|---|---|---|
| 1 | MRSD + FOS | 8.6634 ± 0.11 | 5.8723 ± 0.16 |
| 2 | MRSD + GOS | 8.3231 ± 0.12 | 5.4751 ± 0.12 |
| 3 | MRSD + Lactose | 8.2345 ± 0.13 | 5.5641 ± 0.13 |
| 4 | MRSD + Potato Starch | 8.5432 ± 0.16 | 5.3241 ± 0.11 |
| 5 | MRSD + Inulin | 8.3657 ± 0.13 | 5.5687 ± 0.14 |
| 6 | MRSD + Polydextrose | 8.4587 ± 0.10 | 5.4471 ± 0.11 |
| 7 | MRSD + Dextrose | 8.6574 ± 0.12 | 5.3010 ± 0.13 |

TABLE 11

Effect of *B. coagulans* MTCC 5856 on the viable count of *Clostridium difficile* ATCC 9689

| S. No. | Media composition | *C. difficile* ATCC 9689 alone (cfu/ml) | *B. coagulans* MTCC 5856 + *C. difficile* ATCC 9689 (cfu/ml) |
|---|---|---|---|
| 1 | MRSD + FOS | 8.8754 ± 0.11 | 5.9542 ± 0.13 |
| 2 | MRSD + GOS | 8.6521 ± 0.11 | 5.8965 ± 0.13 |
| 3 | MRSD + Lactose | 8.5624 ± 0.12 | 5.7511 ± 0.11 |
| 4 | MRSD + Potato Starch | 8.8421 ± 0.15 | 5.4771 ± 0.15 |
| 5 | MRSD + Inulin | 8.6524 ± 0.15 | 5.6568 ± 0.11 |
| 6 | MRSD + Polydextrose | 8.7845 ± 0.10 | 5.5472 ± 0.13 |
| 7 | MRSD + Dextrose | 8.8542 ± 0.14 | 5.8303 ± 0.14 |

TABLE 12

Effect of B. coagulans MTCC 5856 on the viable count of Bilophila wadsworthia ATCC 49260

| S. No. | Media composition | B. wadsworthia ATCC 49260 alone (cfu/ml) | B. coagulans MTCC 5856 + B. wadsworthia ATCC 49260 9689 (cfu/ml) |
|---|---|---|---|
| 1 | MRSD + FOS | 8.8564 ± 0.17 | 5.7542 ± 0.13 |
| 2 | MRSD + GOS | 8.7845 ± 0.12 | 5.6965 ± 0.11 |
| 3 | MRSD + Lactose | 8.6598 ± 0.14 | 5.7811 ± 0.12 |
| 4 | MRSD + Potato Starch | 8.7854 ± 0.12 | 5.4171 ± 0.14 |
| 5 | MRSD + Inulin | 8.7524 ± 0.11 | 5.6268 ± 0.14 |
| 6 | MRSD + Polydextrose | 8.7945 ± 0.10 | 5.7972 ± 0.13 |
| 7 | MRSD + Dextrose | 8.8942 ± 0.13 | 5.7303 ± 0.12 |

The results indicated that *Bacillus coagulans* MTCC 5856 significantly reduced the viable colonies of flatus producing microbes *E. coli* ATCC 8739, *Acinetobacter calcoaceticus* ATCC 23055, *Acinetobacter johnsonii* NCIMB9871, *Methanobrevibacter smithii* DSM-861, *Clostridium difficile* ATCC 9689, *Bilophila wadsworthia* ATCC 49260, thereby inhibiting the growth of the aforementioned microbes.

Example 4: Compositions/Formulations Containing *Bacillus coagulans* for Reducing Flatus Tables 13-17, provide illustrative examples of formulations containing *Bacillus coagulans*

TABLE 13

*Bacillus coagulans* Tablet

Active Ingredients

*Bacillus coagulans* MTCC 5856: 2 billion cfu
Plant fibre
Excipients

Microcrystalline cellulose, Colloidal silicon dioxide, Magnesium stearate

TABLE 14

*Bacillus coagulans* Tablet

Active Ingredients

*Bacillus coagulans* MTCC 5856: 2 billion cfu
Plant fibre
Simethicone
Excipients Microcrystalline cellulose, Colloidal silicon dioxide, Magnesium stearate

TABLE 15

*Bacillus coagulans* Capsule

Active Ingredients

*Bacillus coagulans* MTCC 5856: 2 billion cfu
Plant fibre
Excipients

Microcrystalline cellulose

TABLE 16

*Bacillus coagulans* Capsule

Active Ingredients

*Bacillus coagulans* MTCC 5856: 2 billion cfu
Plant fibre
Simethicone
Excipients Microcrystalline cellulose

TABLE 17

*Bacillus coagulans* Powder for gas reduction

Active Ingredients

*Bacillus coagulans* MTCC 5856: 2 billion cfu
Plant fibre
Excipients

Sodium bicarbonate, citric acid, tartaric acid, Polyvinyl pyrrolidone K-30/Hydroxypropyl Cellulose, Lactose/Mannitol, Sucralose/Sodium Saccharin/Aspartame, Flavouring agents, Colouring agents The above formulations are just illustrative examples, any formulation containing the above active ingredient intended for the said purpose will be considered equivalent.

Other modifications and variations to the invention will be apparent to those skilled in the art from the foregoing disclosure and teachings. Thus, while only certain embodiments of the invention have been specifically described herein, it will be apparent that numerous modifications may be made thereto without departing from the spirit and scope of the invention.

We claim:

1. A method for reducing gas formed as a byproduct of microbial fermentation, said method comprising steps of co-culturing the gas producing microbes with a probiotic bacteria *Bacillus coagulans* MTCC 5856, in the presence of a media containing carbohydrate source and prebiotic fibres, to bring about the reduction in gas formation.

2. The method as in claim 1, wherein the probiotic bacteria *Bacillus coagulans* MTCC 5856 per se does not produce substantial gas/flatus when cultured with carbohydrate source and prebiotic fibres.

3. The method as in claim 1, wherein the *Bacillus coagulans* MTCC 5856 is in the form of spore and/or a vegetative cell.

4. The method as in claim 1, wherein the gas producing microbes are selected from the list consisting of *E. coli, Acinetobacter baumannii, Acinetobacter calcoaceticus, Acinetobacter lwoffii, Acinetobacter johnsonii, Methanobrevibacter smithii, Bilophila wadsworthia,* and *Clostridium difficile*.

5. The method as in claim 1, wherein the carbohydrate source and prebiotic fibres are selected from the group consisting of fructo-oligosaccharide (FOS), Galacto-oligosaccharide (GOS), Lactose, potato starch, Inulin, polydextrose and dextrose.

6. A method for inhibiting the growth of gas producing microbes, said method comprising steps of co-culturing the gas producing microbes with a probiotic bacteria *Bacillus coagulans* MTCC 5856, in the presence of a media containing carbohydrate source and prebiotic fibre, to bring about the reduction in the viable colonies of gas producing microbes.

7. The method as in claim 6, wherein the *Bacillus coagulans* MTCC 5856 is in the form of spore and/or a vegetative cell.

8. The method as in claim 6, wherein the gas producing microbes are selected from the list consisting of *E. coli, Acinetobacter baumannii, Acinetobacter calcoaceticus*, and *Acinetobacter lwoffii, Acinetobacter johnsonii, Methanobrevibacter smithii, Bilophila wadsworthia*, and *Clostridium difficile*.

9. The method as in claim 6, wherein the carbohydrate source and prebiotic fibres are selected from the group consisting of fructo-oligosaccharide (FOS), Galacto-oligosaccharide (GOS), Lactose, potato starch, Inulin, polydextrose and dextrose.

* * * * *